US008926570B2

(12) United States Patent
Chung

(10) Patent No.: US 8,926,570 B2
(45) Date of Patent: Jan. 6, 2015

(54) MEDICAMENT DELIVERY DEVICE

(75) Inventor: Kenny Kai Fung Chung, Stockholm (SE)

(73) Assignee: SHL Group AB, Nacka Strand (SE)

(*) Notice: Subject to any disclaimer, the term of this patent is extended or adjusted under 35 U.S.C. 154(b) by 0 days.

(21) Appl. No.: 13/701,506

(22) PCT Filed: May 9, 2011

(86) PCT No.: PCT/SE2011/050582
§ 371 (c)(1),
(2), (4) Date: Apr. 26, 2013

(87) PCT Pub. No.: WO2011/152772
PCT Pub. Date: Dec. 8, 2011

(65) Prior Publication Data
US 2013/0218098 A1    Aug. 22, 2013

Related U.S. Application Data

(60) Provisional application No. 61/350,994, filed on Jun. 3, 2010.

(30) Foreign Application Priority Data

Jun. 3, 2010    (SE) .................................. 1050563-4

(51) Int. Cl.
*A61M 5/315* (2006.01)
(52) U.S. Cl.
CPC ......... *A61M 5/31585* (2013.01); *A61M 5/3157* (2013.01); *A61M 5/31571* (2013.01)
USPC ........................................................ 604/223

(58) Field of Classification Search
USPC ............. 604/68, 71, 133, 135, 187, 218, 224, 604/223
See application file for complete search history.

(56) References Cited

U.S. PATENT DOCUMENTS

| | | | |
|---|---|---|---|
| 4,252,118 A | 2/1981 | Richard et al. | |
| 5,496,293 A | 3/1996 | Huggenberger | |
| 6,086,567 A | 7/2000 | Kirchhofer et al. | |
| 8,007,476 B2* | 8/2011 | Graf et al. | 604/211 |
| 8,376,993 B2* | 2/2013 | Cox et al. | 604/110 |
| 2005/0137534 A1* | 6/2005 | Hommann | 604/224 |
| 2007/0088288 A1* | 4/2007 | Barron et al. | 604/207 |
| 2008/0108953 A1* | 5/2008 | Moser et al. | 604/224 |

(Continued)

FOREIGN PATENT DOCUMENTS

WO    2005/097233 A2    10/2005

OTHER PUBLICATIONS

Swedish Patent Office, Int'l Search Report in PCT/SE2011/050582, Sep. 22, 2011.

(Continued)

*Primary Examiner* — Kami A Bosworth
*Assistant Examiner* — Glen Janson
(74) *Attorney, Agent, or Firm* — Piedmont Intellectual Property

(57) ABSTRACT

The present invention relates to a medicament delivery device that is reliable, safe and intuitive to use and configured to prevent a subsequent dose from being administered before a previously initialized dose has been fully delivered. This is accomplished by mechanically interacting structures arranged as an interface between a lockable delivery button and a release member.

7 Claims, 8 Drawing Sheets

(56) References Cited

U.S. PATENT DOCUMENTS

2010/0010454 A1\* 1/2010 Marshall et al. .............. 604/208
2010/0069845 A1\* 3/2010 Marshall et al. .............. 604/135
2011/0092905 A1\* 4/2011 Cowe ............................ 604/135

OTHER PUBLICATIONS

Swedish Patent Office, Written Opinion in PCT/SE2011/050582, Sep. 22, 2011.

\* cited by examiner

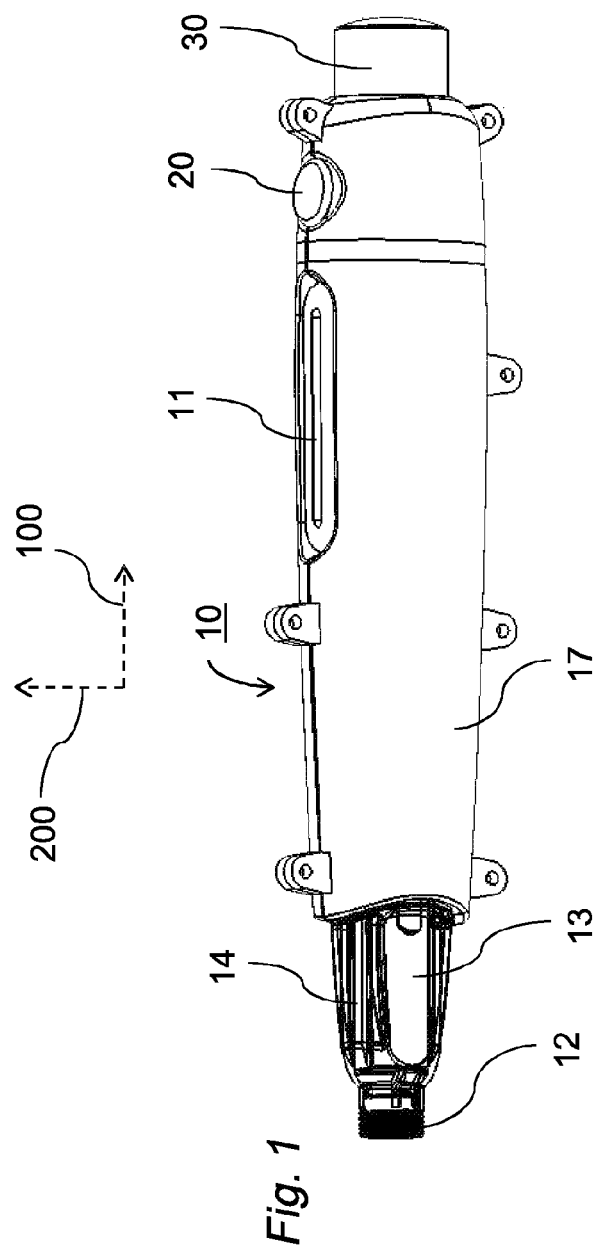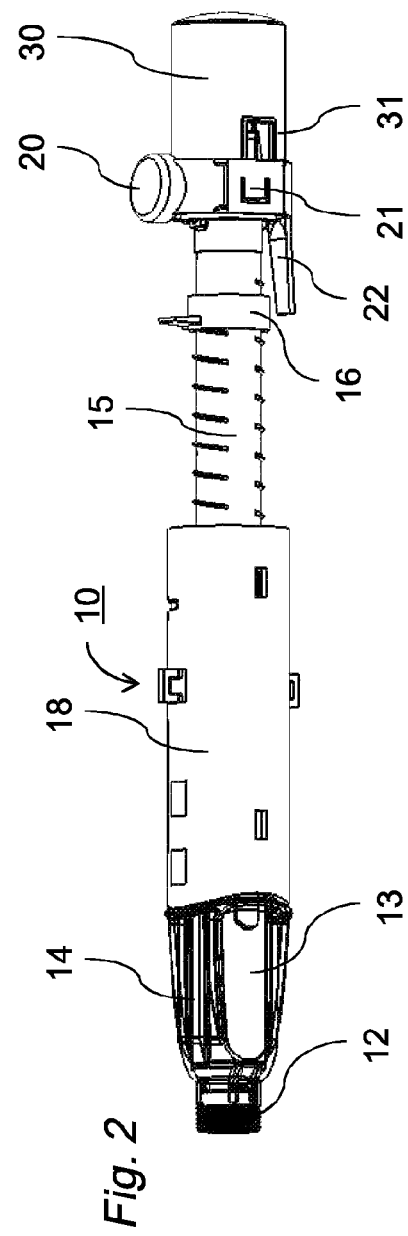
Fig. 1
Fig. 2

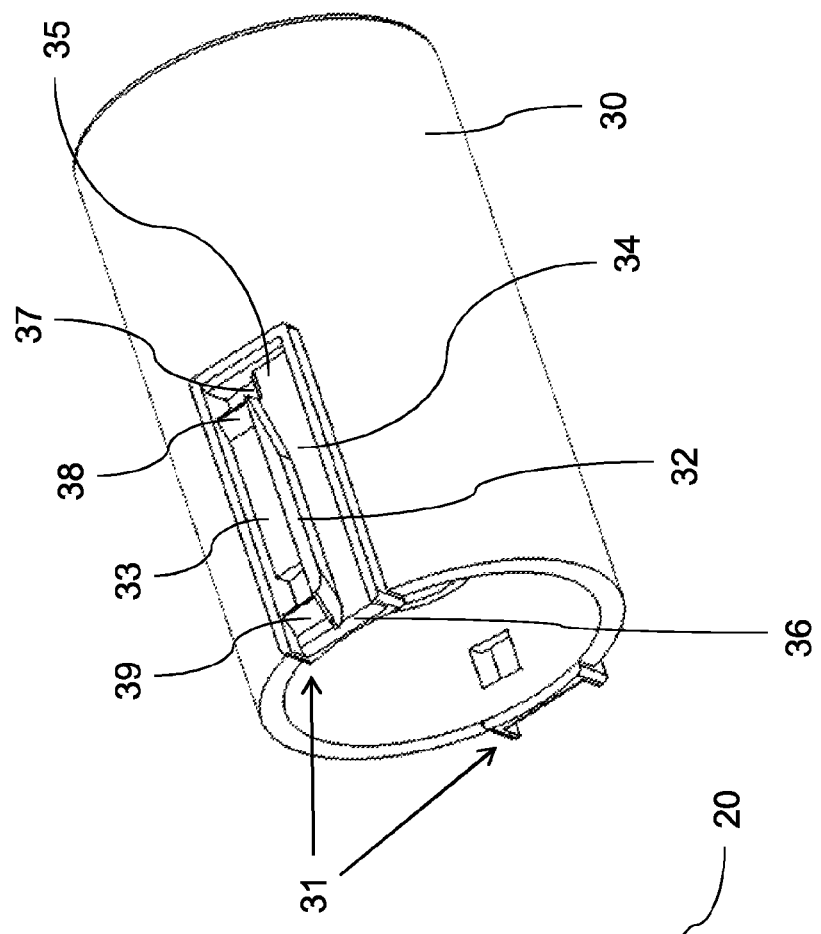
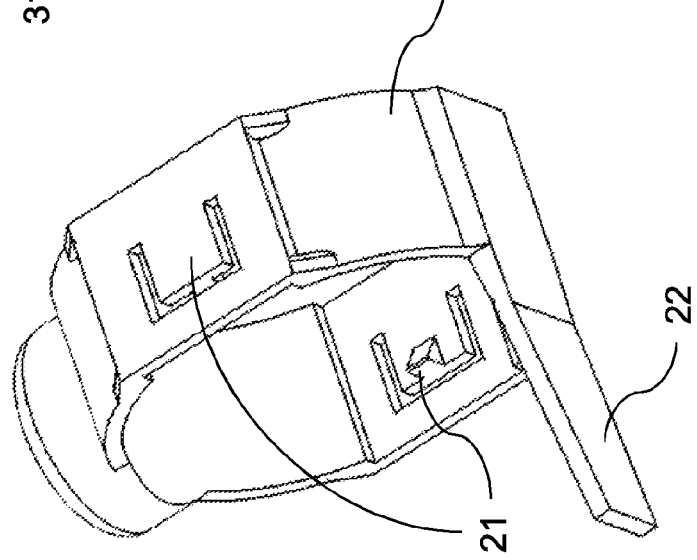
Fig. 4

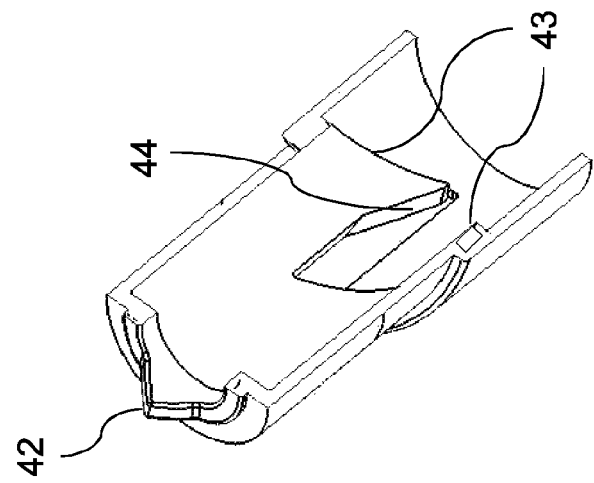
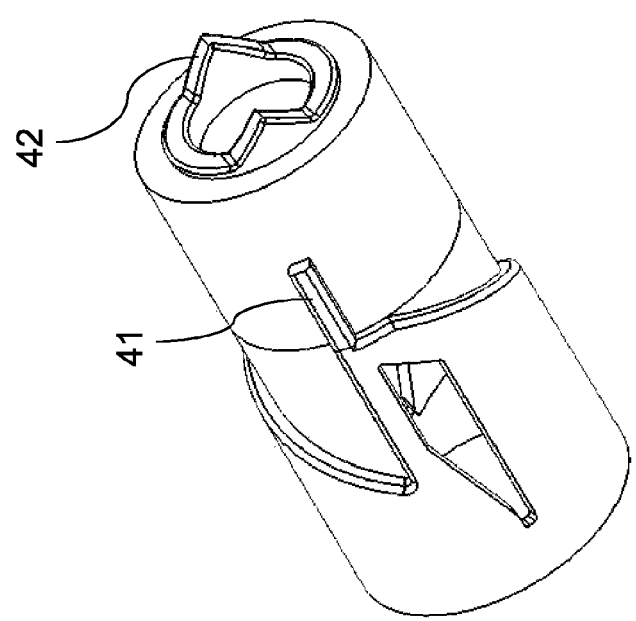

MEDICAMENT DELIVERY DEVICE

TECHNICAL FIELD

The present invention relates to a medicament delivery device for delivering medicament and in particular to a medicament delivery device where safety and handling aspects have been improved by the interaction of a lockable injection button and a release button.

BACKGROUND

Basically a medicament delivery device is a device that is simple to use without the need of performing many steps when an individual has to administer a dose of medicament by himself/herself. This requires a solution able of keeping a medicament delivery device as pre-assembled and ready as possible, in order to deliver the medicament in a measured dosage, without many manual operations or actions. Thus, to minimize the number of steps needed, in order to perform a medicament delivery, some known prior art devices only need to be actuated against the delivery area, without the need of manual actuation, by pressing a button or the like, which causes the medicament delivery device to perform the delivery. There is however a common request for a medicament delivery device which is very easy to use and which can reliably deliver a set dose of a medicament in a safe way.

U.S. Pat. No. 5,925,021 discloses a pen injector device comprising a locking means for locking the actuator knob in a depressed position, a start button for releasing the actuator button and a dosage knob for setting a prescribed dose. U.S. Pat. No. 5,925,021 also comprises electronics, such as sensors and display devices for controlling the injection, for measuring and storing ejected doses and for displaying information to the user. A disadvantage of this prior art is that a dose needs to be set and then injected manually by pushing the actuator button until it stops. In a stressful situation, or if handled by an inexperienced user, the injection may be interrupted mid-way and the button may be released inadvertently. If the button is depressed again, i.e. without adjusting the dosage, a new dose of the previous setting will be initialized, which will lead to the patient receiving an overdose.

There is therefore a need for an arrangement that can provide safe and simple handling both by inexperienced users and in stressful situations. Hence, there is a need for an arrangement where a predetermined dosage is fully delivered, i.e. an arrangement for administering a predetermined dose such that the delivery of a previously initialized dose of medicament has to be fully completed before delivery a subsequent predetermined dose can be initialized. Thus, as can be noted, human handling aspects of the medicament delivery device are crucial and there are several rationales for improving existing solutions.

SUMMARY

An object of the embodiments of the present invention is to provide a medicament delivery device that is reliable, safe and intuitive to use and that does not allow a subsequent dose to be administered before a previously initialized dose has been fully delivered. This is achieved by the main aspect of the invention, wherein a delivery device for delivering predetermined amounts of medicament, comprises a body having an outer housing and an inner housing and having a proximal and an opposite distal end, a cartridge with medicament to be delivered arranged inside said inner housing, said cartridge comprising an opening for expelling said medicament and a stopper movable inside said container, a threaded plunger rod arranged movable inside said body in the longitudinal direction and in contact with said movable stopper, a manually operated push means movable in the longitudinal direction and capable of, upon operation, moving said plunger rod towards said movable stopper, thereby expelling medicament through said opening, and a spring means for biasing said push means towards the distal end of the device, and a first driver and a second driver for transforming a generally linear movement of said push means to a rotational movement of said plunger rod, wherein said transforming means comprises a first set of protruding structures arranged on said first driver cooperating with a set of inclined ledges arranged on said second driver rotatably locked to said plunger rod, wherein in the device comprises a movable release member having a guide member adapted to interact with a guide frame arranged on the outer circumferential surface of the manually operated push means and wherein said guide frame is configured to prevent the delivery of a subsequent dose before a previously initialized dose has been fully administered.

According to a further aspect of the invention the guide frame comprises parallel first and second longitudinally oriented tracks separated by a longitudinally oriented wall element and connected to each other by distal and proximal transversal tracks.

According to a further aspect of the invention the guide member is arranged to project into said tracks.

According to a further aspect of the invention said manually operated push means, in cooperation with said release member, is movably arranged in the longitudinal direction between a depressed position in which the guide member is generally aligned with said distal transversal track and a released position in which the guide member is generally aligned with said proximal transversal track.

According to a further aspect of the invention the release member, in cooperation with said push means, is arranged movable along a transversal direction between a first position in which the guide member is generally aligned with said first track and a second position in which the guide member is generally aligned with said second track.

According to a further aspect of the invention said release member comprises a resilient element and wherein said resilient element is arranged to bias said release member in the transversal direction towards said first position.

According to a further aspect of the invention said distal transversal track comprises a longitudinally aligned ramp that is capable of interacting with said guide member to allow movement of said release member from said first position to said second position.

According to a further aspect of the invention the first longitudinally oriented track is arranged with a first transversally aligned step ramp at a distal end of said wall element and a second transversally aligned step ramp at a proximal end of said wall element, wherein said first and second step ramps are capable of interacting with said guide member to allow movement of said manually operated push means towards the depressed position and to prevent said manually operated push means from return movement towards the released position.

According to a further aspect of the invention said guide member is arranged on a flexible tongue of the release member.

By the disclosed medicament delivery device mis-delivery of a dose of medicament is avoided. The delivery of a dose of medicament may be interrupted, but a subsequent dose cannot be administered until a previously initialized dose has been completely delivered. The described advantages are possible due to the fact that it is impossible to reset the manually operated push means, such as an injection button, for a subsequent dose without first depressing it completely to eject the remainder of the current, initialized dose.

These and other aspects and advantages of the present invention will become apparent from the following detailed description and from the accompanying drawings.

BRIEF DESCRIPTION OF THE DRAWINGS

In the following description of embodiments of the invention, reference will be made to the accompanying drawings of which:

FIG. 1 is a perspective view of an exemplary medicament delivery device according to the invention.

FIG. 2 shows, in perspective, a view inside the medicament delivery device of FIG. 1 without the outer housing.

FIG. 4 illustrates, in perspective, an exploded view of the manually operated push means and the release member of the medicament delivery device of FIG. 1.

FIG. 6A illustrates, in perspective, a second drive member of the medicament delivery device of FIG. 1.

FIG. 6B illustrates a cross section of FIG. 6A.

DETAILED DESCRIPTION

Figure 3:
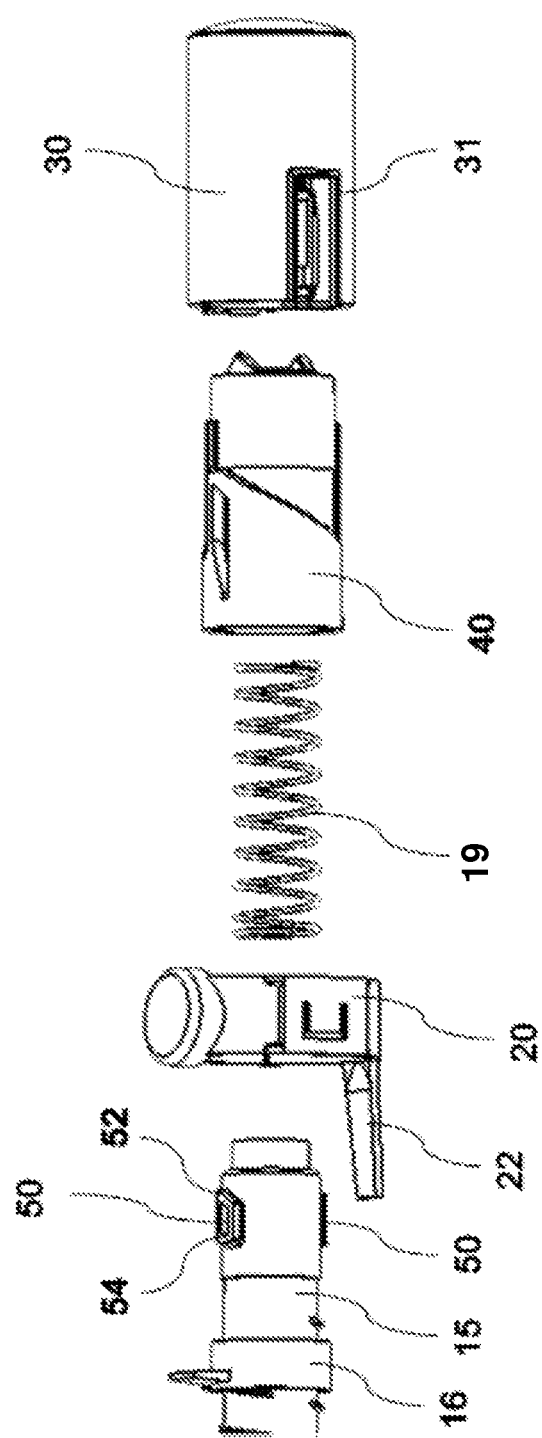
FIG. 3 illustrates, in perspective, an exploded view of the components of the actuating mechanism of the medicament delivery device of FIG. 1.

Embodiments of the present invention will now be described in detail. As should be noted in the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

According to the main aspect of the invention, a medicament delivery device for delivering predetermined amounts of medicament comprises a body having an outer housing and an inner housing, and having a proximal and an opposite distal end, a cartridge with medicament to be delivered arranged inside said inner housing, said cartridge comprising an opening for expelling said medicament and a stopper movable inside said container, a threaded plunger rod arranged movable inside said body in the longitudinal direction and in contact with said movable stopper, a manually operated push means movable in the longitudinal direction and capable of, upon operation, moving said plunger rod towards said movable stopper, thereby expelling medicament through said opening, and a spring means for biasing said push means towards the distal end of the device, and a first driver and a second driver for transforming a generally linear movement of said push means to a rotational movement of said plunger rod, wherein said transforming means comprises a first set of protruding structures arranged on said first driver cooperating with a set of inclined ledges arranged on said second driver rotatably locked to said plunger rod, wherein in the device comprises a movable release member having a guide member adapted to interact with a guide frame arranged on the outer circumferential surface of the manually operated push means and wherein said guide frame is configured to prevent the delivery of a subsequent dose before a previously initialized dose has been fully administered.

According to a further aspect of the invention the guide frame comprises parallel first and second longitudinally oriented tracks separated by a longitudinally oriented wall element and connected to each other by distal and proximal transversal tracks.

An exemplary embodiment of the present invention is shown in the FIGS. 1-8. The exemplary embodiment shown in the figures is a medicament injector for dual medicament cartridges but is not restricted to it. FIG. 1 is a perspective view of exemplary components of a complete medicament delivery device 10 according to the invention. FIG. 1 illustrates the pre-assembled medicament delivery device 10 extending in a longitudinal direction 100. Some of the components of the device can be movable in a transversal direction 200 which is orthogonal to the longitudinal direction 100.

The exemplary delivery device comprises an outer housing 17 arranged with a first view window 11 for indicating the remaining amount of medicament. A proximal end of the cartridge container 14 projects from the proximal end of the outer housing 17. The cartridge container 14 is arranged with a second view window 13 for a user to verify that medicament contents (not shown) have been mixed. The cartridge container 14 is also arranged at its proximal end with engaging means 12 as e.g. threads but not restricted to it, such that a delivery member can be connected. The delivery member may be a needle, a nozzle, a mouth piece, or the like. At the distal part of the outer housing 17 a release member 20 is movably arranged in the transversal direction 200 and a manually operated push means 30, e.g. a push button, is movably arranged in the longitudinal direction 100.

FIG. 2 is a perspective view that illustrates the medicament delivery device 10 without the outer housing 17 (FIG. 1). An inner housing 18 is arranged to receive a distal part of the cartridge container 14 by threaded engagement between the outer distal surface of the cartridge container 14 and an inner surface of the inner housing 18. Connected to the distal part of the inner housing 18 is a first driver 15, rotatably arranged but movably locked in a longitudinal direction in relation to the housings 17 and 18. By a structural interface (not shown) between the inner distal annular surface of the inner housing 18 and a proximal annular surface of the first driver 15, reverse rotation of the first driver 15 is prevented as the manually operated push means 30 moves towards a released position (to be explained below). The first driver 15 is arranged with outer threads that engage inner threads of an indicator means 16. Since the indicator means 16 is rotatably locked to the outer housing 17, rotation of the first driver 15 is transformed into longitudinal movement of the indicator means 16 in relation to the outer housing 17 for indicating the remaining amount of medicament through the first view window 11 (FIG. 1).

The release member 20, as shown in FIG. 2, may have an annular form and be arranged in close proximity around the manually operated push means 30. A guide member 21 protrudes radially inwards from the release member 20 to engage a guide frame 31 arranged on the outside circumferential surface of the manually operated push means 30. The part of the release member 20 that is operated by a patient/user and that protrudes through the outer housing 17, as shown in FIG. 1, may be shaped as a push button. The release member is actuated by a user in order to unlock the device for delivery of a dose of medicament. After actuation, the release member 20 is returned by a resilient member 22 that is arranged in a transversally biased position, abutting the inside of the outer housing 17. In the exemplary embodiment, the resilient member 22 depicted in FIG. 2 is in the shape of a flexible finger of the release member, but it could just as well be any other kind of flexible member, e.g. a coil spring. The effect might also be attained by a native resilience of the material and/or the shape of the release member 20 itself. The cooperation between the guide member 21 and the guide frame 31 ensures the safe and simple delivery of complete doses of medicament, which will be explained in detail below.

Figure 9:
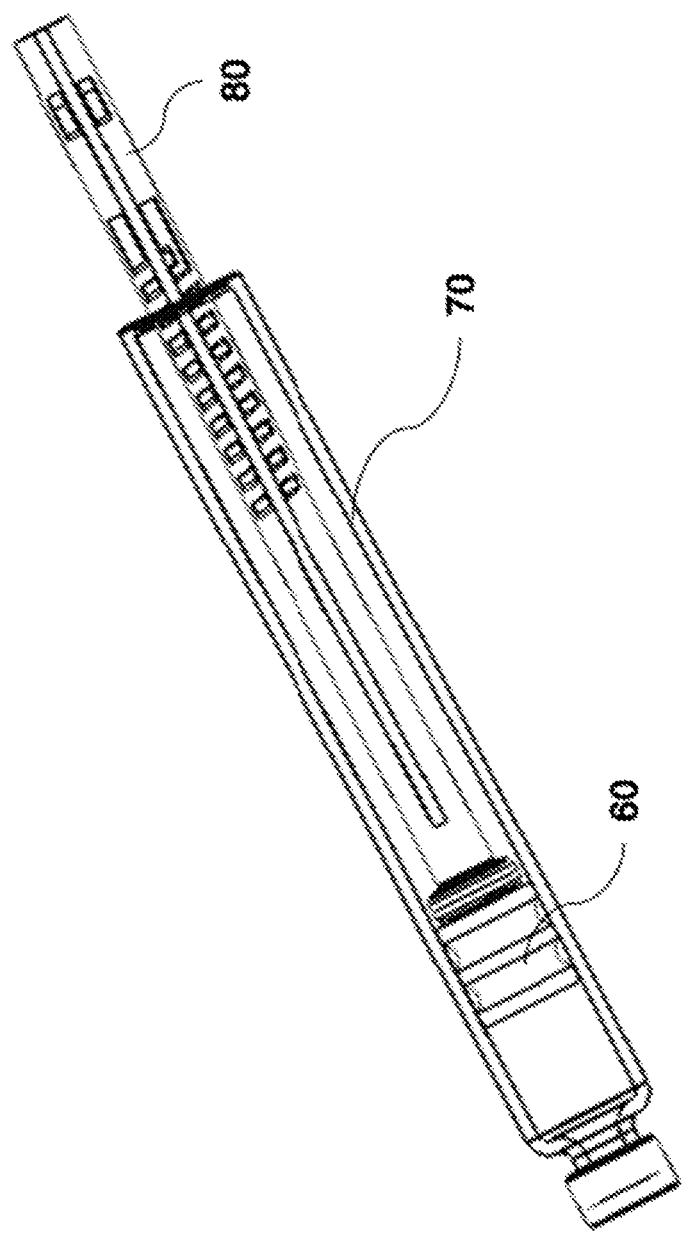
FIG. 9 illustrates a threaded plunger rod, cartridge, and stopper.

The general function of the exemplary medicament delivery device, as shown in FIGS. 1 and 2, is described by the following steps. The device is operated by first unlocking and releasing the manually operated push means 30 by depressing the release member 20 in the transversal direction and then actuating the push means 30 in the longitudinal direction. A second driver 40 (FIG. 3) is arranged coaxially on the distal part of the first driver 15. The distal end of the second driver is arranged coaxially within the manually operated push means 30, acting to transform the longitudinal movement of the push means 30 to rotational movement of the first driver 15, which mechanism will be explained below. A plunger rod 80 (shown in FIG. 9) is slidably arranged, but rotatably locked inside the first driver 15 and extends from the inside of the first driver 15 to threaded engagement with a threaded opening at a distal annular surface of the inner housing 18. The proximal end of the plunger rod extends into a cartridge 70 (shown in FIG. 9) which is positioned in the cartridge container 14 and is abutting to a movable stopper 60 (shown in FIG. 9) that acts on medicament within the container to drive it towards the delivery member as the plunger rod is actuated by the rotation of the first driver 15. Since the plunger rod is rotatably locked to the first driver 15 and since the inner housing 18 is fixed to the outer housing, the relative rotation of the first driver 15 in relation to the inner housing 18, urges the plunger rod in the longitudinally proximal direction by the threaded engagement between the plunger rod and the inner housing 18.

The exemplary embodiment, as shown in FIG. 3, is an exploded view of the main components of the invention at the distal end of the medicament delivery device. The first driver 15 is rotatable, but movably locked along a longitudinal axis. A spring means 18 is arranged in permanent compression between an annular ledge on the distal end of the first driver 15 and on an annular inner surface of the distal end of the second driver 40. The second driver is movable, and to a limited extent rotatable, along the longitudinal axis. The spring means 18 forces the second driver 40 against the inner surface of the distal end of the manually operated push means 30. The manually operated push means 30 is movable along a longitudinal axis. The release member 20, which is transversally movable, is arranged coaxially with the push means 30 and aligned with the guide frame 31 for the interaction between the release member 20 and the push means 30. The operation of the exemplary embodiment of FIG. 3 will be explained below.

FIG. 4 shows a perspective view of an exemplary embodiment of the manually operated push means 30 and the release member 20. In order to obtain a medicament delivery device that is safe and simple to handle in accordance with the invention it is necessary to have the device operate sequentially in steps. Therefore the manually operated push means 30 is arranged with at least one guide frame 31, such as two guide frames positioned opposite to each other on the circumferential surface of the push means. The release member 20 is arranged with at least one guide member 21, positioned to cooperate with the at least one guide frame 31.

The guide frame 31 comprises a first longitudinally oriented track 33 that runs parallel to a second longitudinally oriented track 34. They are separated by a longitudinally oriented wall element 32 and connected to each other by a distal transversal track 35 and a proximal transversal track 36. The term track should be interpreted in its widest sense as a path relative to which the guide member 21 may move in a substantially confined manner, i.e. without deviating from the track. Different solutions to tracks are conceivable. The exemplary embodiment of FIG. 4 shows a guide frame having walls that protrude radially from the surface of the manually operated push means 30 and wherein the proximal transversal track 36 is open towards the proximal side. Since the guide member 21 is arranged on the release member 20, which is movably confined transversally by the outer housing 17, the guide member 21 is still aligned with either of the longitudinal tracks 33, 34 even if it should be positioned proximally to the proximal transversal track 36, i.e. proximally to the guide frame 31 as a whole.

The distal transversal track 35 comprises a longitudinally aligned ramp 37. The first longitudinally oriented track 33 comprises a first transversally aligned step ramp 38 at a distal end of the wall element 32 and a second transversally aligned step ramp 39 at a proximal end of the wall element 32. The purpose of these ramps will be explained in conjunction with FIGS. 5A-F.

The guide member 21 may be arranged as a protrusion, e.g. in the form of a step ramp, directed radially inwardly to protrude into the tracks of the guide frame 31 for interaction therewith. Said protrusion being arranged on at least one flexible tongue, or cut-out, on the circumference of the release member 20. The manually operated push means 30 is movable in the longitudinal direction while the release member 20 is movable in the transversal direction. The manually operated push means 30 is arranged to be movable in the longitudinal direction between a depressed position in which the guide member 21 is generally aligned with said distal transversal track 35 and a released position in which the guide member 21 is generally aligned with said proximal transversal track 36. The release member 20 is movably arranged in the transversal direction between a first position in which the guide member 21 is generally aligned with said first track 33 and a second position in which the guide member is generally aligned with said second track 34.

The manually operated push means 30 is permanently longitudinally biased in the distal, released, direction by the spring means 18 (FIG. 3) and the release member 20 is permanently transversally biased towards the first position by the resilient member 22. Force is required by the user of the device to displace the release member 20 and the push means 30 against their respective biasing directions.

Figure 5A:
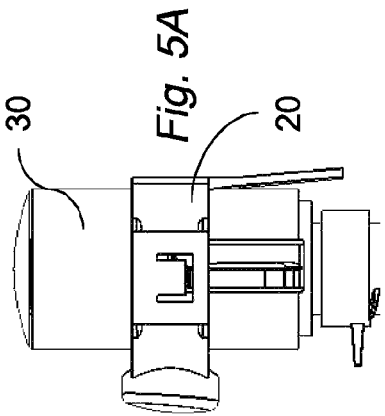
FIGS. 5A-5F illustrates a sequence of the manually operated push means and the release member in different states of operation.

Referring now to FIGS. 5A-F, illustrated is a sequence of steps that show the operation of the medicament delivery device 10 and the interaction between the manually operated push means 30 and the release member 20. In FIG. 5A the medicament delivery device 10 is in a locked position in which the push means 30 is in the depressed position and is locked from movement towards the released position by an engagement between the guide element 21 and the first transversally aligned step ramp 38. The release member is stable in the first position due to the permanent spring bias of the resilient member 22. To unlock the medicament delivery device 10, the user has to displace the release member 20 towards the second position by exerting a transversal force on the release member 20 that overcomes the spring bias of the resilient member 22. A certain additional frictional force is required to overcome the resistance presented by the longitudinally aligned ramp 37 in order to lower the risk of accidental unlocking of the device.

Figure 5B:
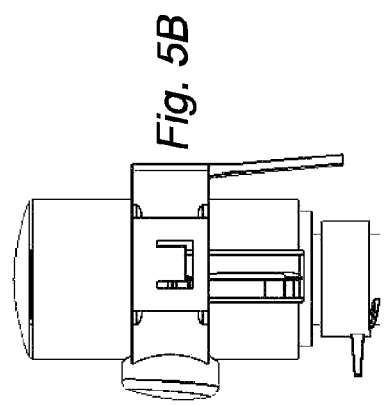
Figure 5C:
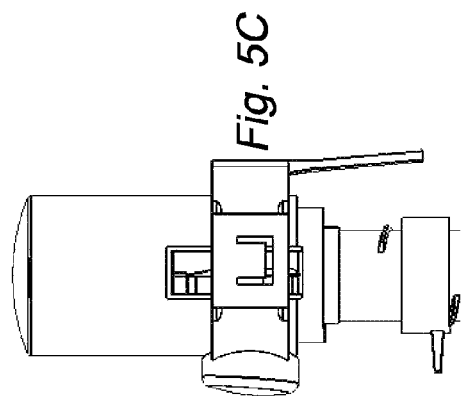

Turning to FIG. 5B, illustrated is a state where the medicament delivery device 10 has been unlocked wherein the release member 20 is still held in the second position by the user after displacement from the first position (FIG. 5A). The manually operated push means is biased towards the released, distal, position by the spring means 18. Consequently the push means 30 is displaced distally towards the released position. FIG. 5C shows the push means 30 moving distally towards the released position.

Figure 5D:
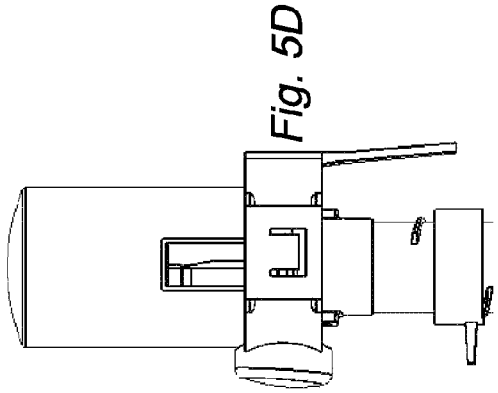
Figure 5E:
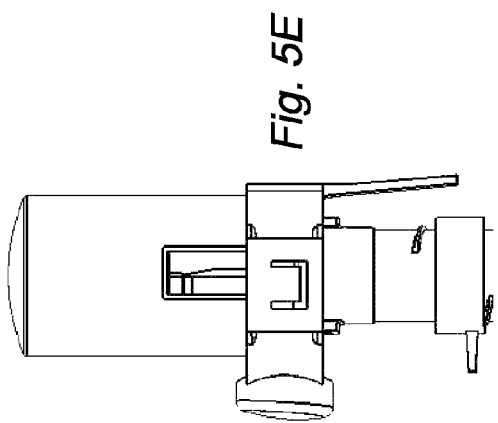

As illustrated in FIG. 5D, the push means 30 has reached the released position while the user is still holding the release member 20 in the second position. As he/she lets go of the release member 20, it is returned to the first position by the bias of the resilient member 22, as seen in FIG. 5E. Referring back to the FIG. 5C, if the user drops the release member 20 while the push means 30 is still moving, the wall element 32 will still hold the guide member 21 and the release member 20 in the second position, thereby preventing return movement of the release member 20 to the first position. When the push means 30 reaches the released position, the guide element 21 aligns with the proximal transversal track 36, allowing return movement of the release member 20.

Figure 5F:
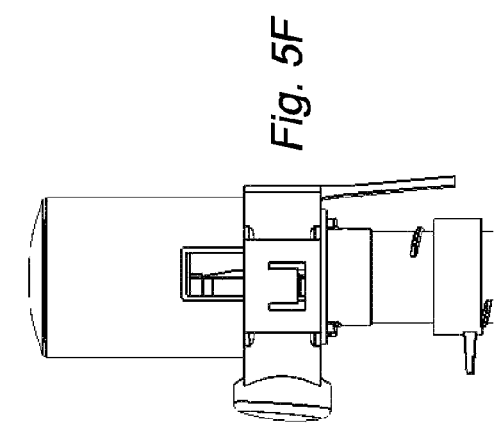

FIG. 5F illustrates the push means 30 and the release member 20 after initial depression of the push means 30. As the push means 30 is proximally depressed as shown in FIG. 5F, the second transversally aligned step ramp 39 passes the guide member 21, making an audible clicking sound as the guide member 21 and the second step ramp 39 snap into locking engagement with each other. The only possible movement of the guide member 21 and the push means 30 hereafter is the continued depression of the push means 30. The purpose of the second step ramp 39, apart from giving an audible indication to the user, is to prevent the push means 30 from returning to the released position and thereby resetting for a subsequent dose before the current, previously initialized dose has been fully administered. The mechanism for resetting the device is explained in conjunction with FIGS. 6-8. When completely depressed, the push means is back at the depressed position, shown in FIG. 5A. As the first transversally aligned step ramp 38 passes the guide member 21, an audible sound is made as the guide member 21 and the first step ramp 38 snap into locking engagement with each other, locking the device and also indicating to the user that the dose has been fully delivered.

Although the main aspects of the invention concern the interaction between the release member 20 and the manually operated push means 30, as exemplified by FIGS. 4 and 5A-F, a crucial part of the operation of the medicament delivery device 10 is the interaction between the first driver 15 and the second driver 40. One such exemplary embodiment is shown in FIG. 6-8.

FIG. 6A shows a perspective view of the second driver 40, comprising a protruding, longitudinal rib 41 arranged on the outer circumferential surface. Inclined ramps 42 are arranged on the distal end surface of the second driver 40. FIG. 6B illustrates a cross section of the second driver 40 wherein its inner circumferential surface comprises inside inclined ledges 43 facing generally the proximal direction and return ledges 44 facing generally in the distal direction.

The inclination of the ledges and number of ledges depend on the amount of medicament to be delivered per dose and are set to predetermined values during manufacturing of the second driver 40. In the illustrated embodiment in FIG. 6B, for instance, there are two oppositely arranged inclined ledges 43 that correspond to two protruding structures 50 on the outer circumference of the first driver 15, exemplified in FIG. 3.

Figure 7:
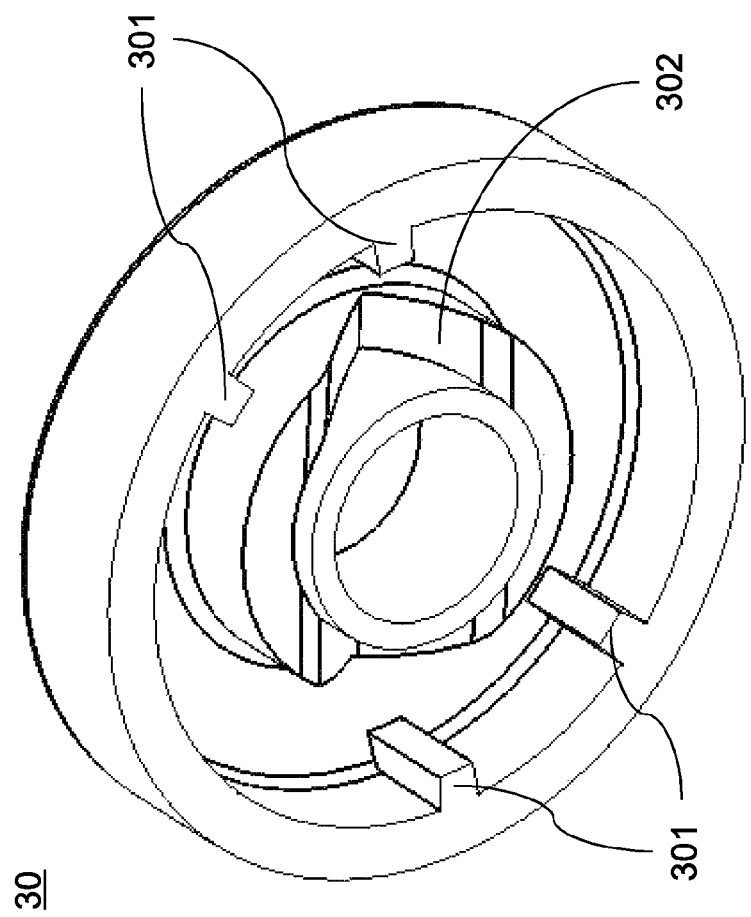
FIG. 7 illustrates a cross section of the manually operated push means of the medicament delivery device of FIG. 1.
Figure 8:
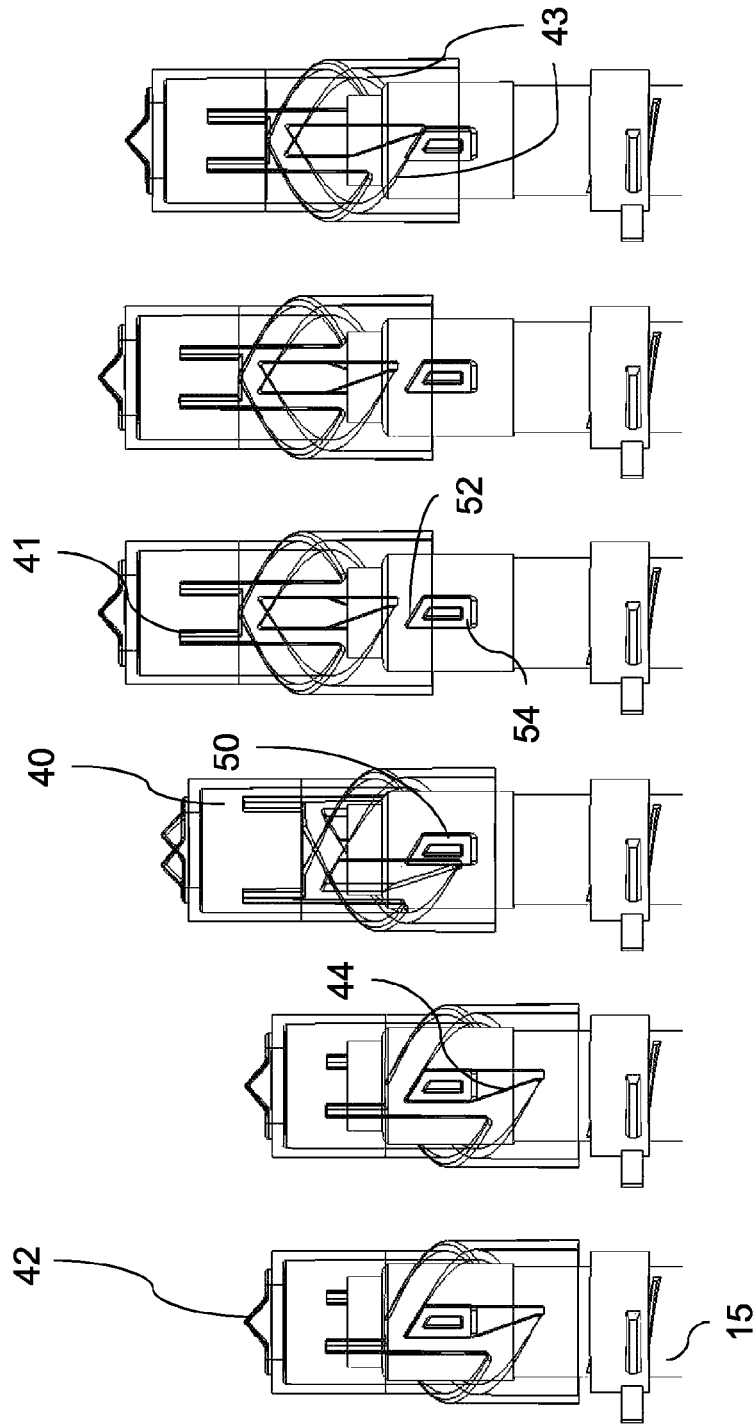
FIGS. 8A-8F illustrate, in a sequence of transparent views, the cooperation of a second drive member and a first drive member.

FIG. 7 is a cross section of the manually operated push means 30. Longitudinal protruding strips 301 (FIG. 7) are arranged on the inside circumferential surface. A seat 302 is arranged on the inner proximally directed surface of the manually operated push means 30.

The operation of the first and second driver is best described by the sequence of drawings illustrated in FIGS. 8A-F, which is a sequence of transparent views of the second driver 40 and the first driver 15 that correspond to the sequence of FIGS. 5A-F. FIG. 8A represents the locked position of the medicament delivery device 10, showing the protruding structure 50 of the first driver at the distal end of the inclined ledge 43. Due to the depressed position of the manually operated push means 30 (not shown) the inclined ramps 42 arranged on the distal end of the second driver are pressed into the seat 302 (FIG. 7) by the force of the spring means 18 (not shown), rotationally locking the second driver 40.

FIGS. 8B-C show that the actuation of the release member 20 towards the second position does not directly affect the drivers (FIG. 8B), but as the push means 30 is displaced towards the released position by the spring means 18, the force of the inclined ramps 42 against the seat 302 is relaxed, allowing the return ledge 44 to slide against the proximal inclined surface 54 of the first driver 15. This rotates the second driver 40 in relation to the first driver 15 and the push means 30. The rotation is limited by the longitudinal rib 41 of the second driver 40 that is loosely confined between the longitudinally protruding strips 301 (FIG. 7) on the inside circumferential surface of the push means 30. Reverse rotation of the first driver 15 during this phase is prevented by the interaction of a structural interface, e.g. a kind of ratchet interface, between the inner distal annular surface of the inner housing 18 and a proximal annular surface of the first driver 15 (not shown).

Referring to FIG. 8D, as the proximal end of the return ledge 44 slides past the protruding structure 50 and the second driver 40 reaches the released position, the inclined ramps 42 are, again, urged against the seat 302, making the second driver 40 rotate back in relation to the first driver 15 and the push means 30, aligning the distal inclined surface 52 with the proximal end of the inclined ledge 43.

FIG. 8E represents the state where the release member 20 is returned to the first position (not shown).

In FIG. 8F the user is pressing the push means 30 (not shown) to start expelling a dose of medicament. This causes the inclined ledge 43 second driver of the second driver 40 to engage the distal inclined surface 52 of the first driver 15, resulting in rotation of the latter. The second driver is rotationally locked due to the engagement between the inclined ramps 42 and the seat 302. As the first driver 15 rotates, the plunger rod (not shown) also rotates. The motion of the plunger rod urges a stopper (not shown) to expel medicament through the delivery member. If the push means 30 is dropped by the user at some point during medicament delivery, the engagement between the inclined ledge 43 and the inclined surface 52 is relaxed, but the first driver 15 remains stationary since no force is acting on it. Therefore it is possible to resume and complete the delivery of the dose at any time. The push means 30, and consequently the second driver 40, have to be fully depressed, as illustrated in FIG. 8A, before a subsequent dose can be initialized.

The present invention is not limited to the above-described preferred embodiment. Various alternatives, modifications and equivalents may be used. Therefore, the above embodiment should not be taken as limiting the scope of the invention, which is defined by the appended claims.

The invention claimed is:

1. A device for delivering predetermined amounts of medicament, comprising:
   a body having an outer housing, an inner housing, a proximal end, and an opposite distal end;
   a cartridge having medicament to be delivered disposed in the inner housing, the cartridge comprising an opening for expelling the medicament and a stopper movable inside the cartridge;
   a threaded plunger rod movably disposed in the body in a longitudinal direction and in contact with the stopper;
   a manually operated push device movable in the longitudinal direction and configured to move, upon operation, the plunger rod toward the stopper, thereby expelling medicament through the opening;
   a spring device configured to bias the push device toward the distal end of the device;
   a first driver and a second driver configured to transform a generally linear movement of the push device into a rotational movement of the plunger rod, wherein the first driver comprises a set of protruding structures configured to cooperate with a set of inclined ledges on the second driver, and the first driver is rotatably locked to the plunger rod;
   a guide frame, comprising first and second longitudinally oriented parallel tracks separated by a longitudinally oriented wall and directly connected to each other around the wall by distal and proximal transversal tracks, wherein the guide frame is disposed on an outer circumferential surface of the push device; and
   a transversally movable unitary release member having a guide member configured to interact with the guide frame, wherein the release member, in cooperation with the push device, is movable in a transversal direction between a first position, in which the guide member is generally aligned with the first longitudinally oriented track, and a second position, in which the guide member is generally aligned with the second longitudinally oriented track, and the guide frame is configured to prevent delivery of a subsequent dose before a previous dose has been fully delivered.

2. The device of claim 1, wherein the guide member is arranged to project into any of the proximal track, the distal track, and the first and second longitudinally oriented tracks.

3. The device of claim 1, wherein the push device, in cooperation with the release member, is movable in the longitudinal direction between a depressed position, in which the guide member is generally aligned with the distal transversal track, and a released position, in which the guide member is generally aligned with the proximal transversal track.

4. The device of claim 3, wherein the first longitudinally oriented track includes a first transversally aligned step ramp at a distal end of the wall and a second transversally aligned step ramp at a proximal end of the wall, the first and second step ramps are configured to interact with the guide member to allow movement of the push device toward the depressed position and to prevent the push device from return movement toward the released position.

5. The device of claim 1, wherein the distal transversal track comprises a longitudinally aligned ramp configured to interact with the guide member to allow movement of the release member from the first position to the second position.

6. A device for delivering predetermined amounts of medicament, comprising:
   a body having an outer housing, an inner housing, a proximal end, and an opposite distal end;
   a cartridge having medicament to be delivered disposed in the inner housing, the cartridge comprising an opening for expelling the medicament and a stopper movable inside the cartridge;
   a threaded plunger rod movably disposed in the body in a longitudinal direction and in contact with the stopper;
   a manually operated push device movable in the longitudinal direction and configured to move, upon operation, the plunger rod toward the stopper, thereby expelling medicament through the opening;
   a spring device configured to bias the push device toward the distal end of the device;
   a first driver and a second driver configured to transform a generally linear movement of the push device into a rotational movement of the plunger rod, wherein the first driver comprises a set of protruding structures configured to cooperate with a set of inclined ledges on the second driver, and the first driver is rotatably locked to the plunger rod;
   a guide frame, comprising first and second longitudinally oriented parallel tracks separated by a longitudinally oriented wall and connected to each other by distal and proximal transversal tracks, wherein the guide frame is disposed on an outer circumferential surface of the push device; and
   a transversally movable unitary release member having a guide member configured to interact with the guide frame, wherein the release member, in cooperation with the push device, is movable in a transversal direction between a first position, in which the guide member is generally aligned with the first longitudinally oriented track, and a second position, in which the guide member is generally aligned with the second longitudinally oriented track, and the guide frame is configured to prevent delivery of a subsequent dose before a previous dose has been fully delivered; and the release member comprises a resilient element, and the resilient element is configured to bias the release member in the transversal direction toward the first position.

7. A device for delivering predetermined amounts of medicament, comprising:
   a body having an outer housing, an inner housing, a proximal end, and an opposite distal end;
   a cartridge having medicament to be delivered disposed in the inner housing, the cartridge comprising an opening for expelling the medicament and a stopper movable inside the cartridge;
   a threaded plunger rod movably disposed in the body in a longitudinal direction and in contact with the stopper;
   a manually operated push device movable in the longitudinal direction and configured to move, upon operation, the plunger rod toward the stopper, thereby expelling medicament through the opening;
   a spring device configured to bias the push device toward the distal end of the device;
   a first driver and a second driver configured to transform a generally linear movement of the push device into a rotational movement of the plunger rod, wherein the first driver comprises a set of protruding structures configured to cooperate with a set of inclined ledges on the second driver, and the first driver is rotatably locked to the plunger rod;

a guide frame, comprising first and second longitudinally oriented parallel tracks separated by a longitudinally oriented wall and connected to each other by distal and proximal transversal tracks, wherein the guide frame is disposed on an outer circumferential surface of the push device; and a transversally movable unitary release member having a guide member configured to interact with the guide frame, wherein the release member, in cooperation with the push device, is movable in a transversal direction between a first position, in which the guide member is generally aligned with the first longitudinally oriented track, and a second position, in which the guide member is generally aligned with the second longitudinally oriented track, and the guide frame is configured to prevent delivery of a subsequent dose before a previous dose has been fully delivered; and the guide member is arranged on a flexible tongue of the release member.

* * * * *